(12) United States Patent
Rathjen et al.

(10) Patent No.: US 7,597,444 B2
(45) Date of Patent: Oct. 6, 2009

(54) OPHTHALMOLOGICAL DEVICE

(75) Inventors: Christian Rathjen, Bremen (DE);
Frank Ziemer, Port (CH)

(73) Assignee: Ziemer Holding AG (CH)

( * ) Notice: Subject to any disclaimer, the term of this patent is extended or adjusted under 35 U.S.C. 154(b) by 184 days.

(21) Appl. No.: 11/822,401

(22) Filed: Jul. 5, 2007

(65) Prior Publication Data

US 2008/0192783 A1 Aug. 14, 2008

(30) Foreign Application Priority Data

Jul. 21, 2006 (EP) .................................. 06405317

(51) Int. Cl.
*A61B 3/10* (2006.01)
(52) U.S. Cl. ....................................... 351/221; 351/210
(58) Field of Classification Search ................. 351/200, 351/205, 210, 212, 221, 247
See application file for complete search history.

(56) References Cited

U.S. PATENT DOCUMENTS 5,975,697 A * 11/1999 Podoleanu et al. .......... 351/206
2007/0282312 A1 * 12/2007 Rathjen .......................... 606/4

* cited by examiner

*Primary Examiner*—Huy K Mai

(57) ABSTRACT

An ophthalmological device (1) comprises a controllable optical correction element (14) for the variable modulation of the wavefront of deflected femtosecond laser pulses. A control module (13) controls the correction element (14) as a function of the deflection of the femtosecond laser pulses in such a way that the femtosecond laser pulses are focused into an image area, arranged around the optical axis (z) of the light projection module (11), on a defined treatment surface. It is possible by means of the adaptive and dynamic modulation of the wavefront of the deflected laser pulses for the laser pulses to be focused onto the treatment surface in an enlarged image area in conjunction with unchanged projection optics of the light projection module (11) such that the image field is enlarged in conjunction with an unchanging compact design of a light projection module (11) suitable for manual application.

13 Claims, 3 Drawing Sheets

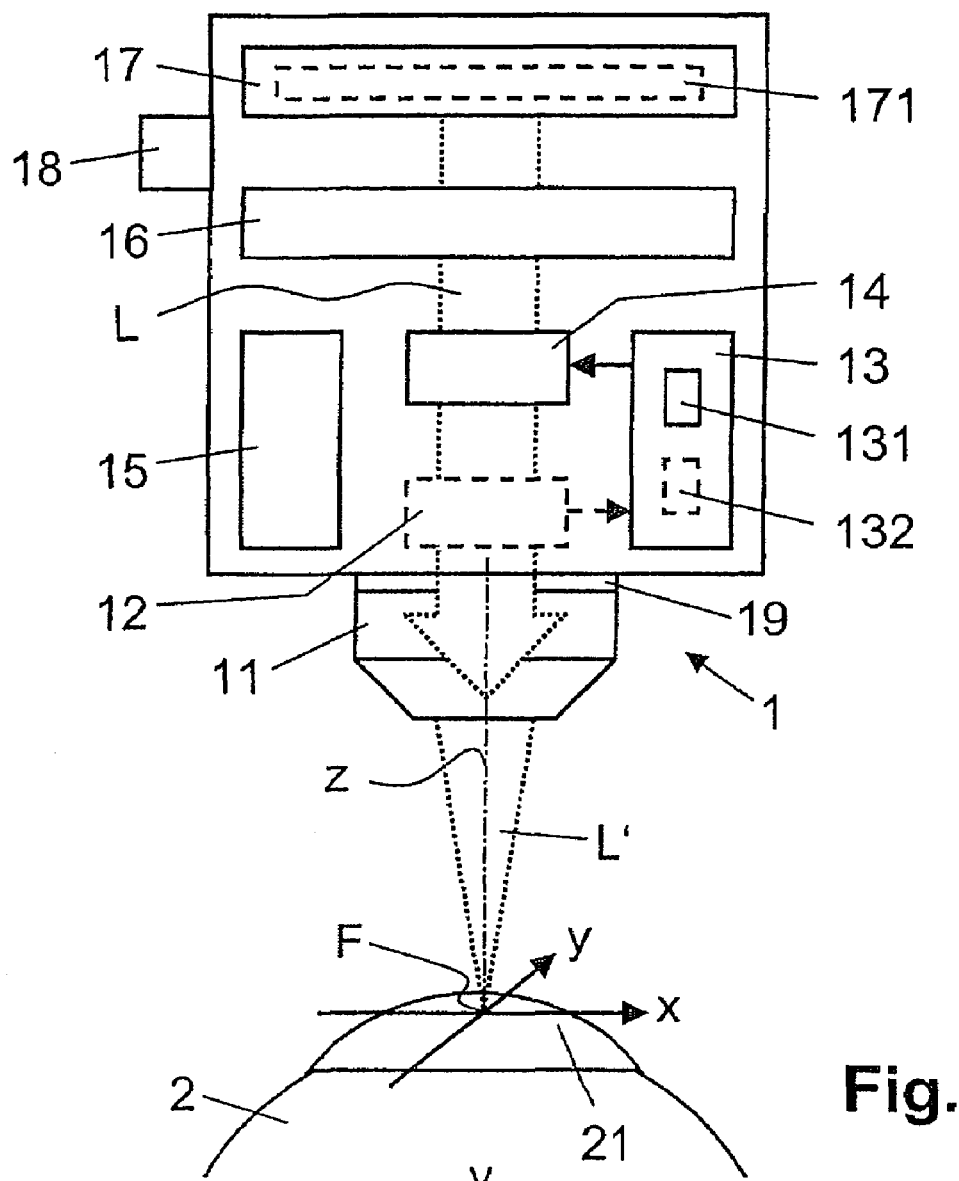
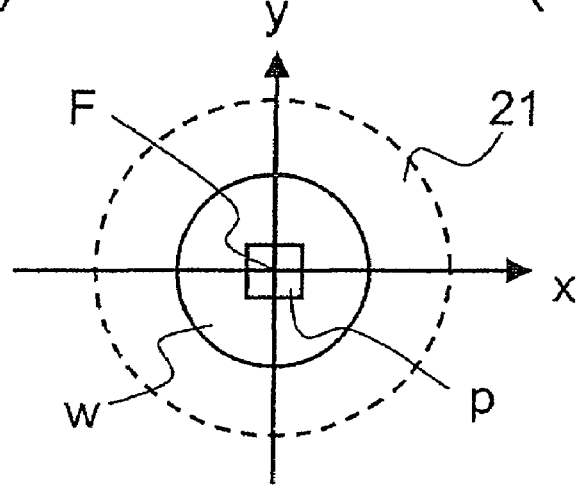
Fig. 1a
Fig. 1b

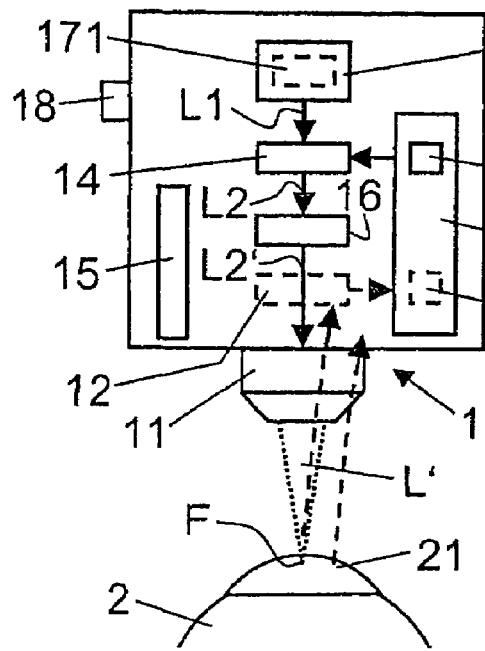
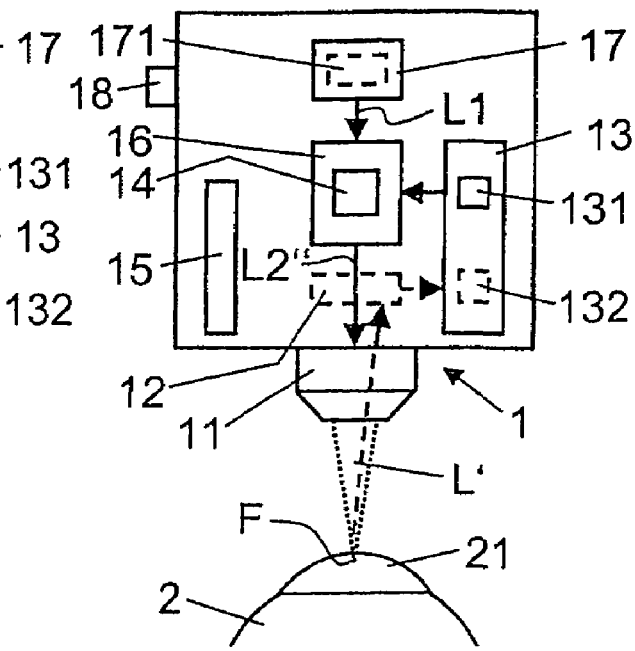
Fig. 2a  Fig. 2b
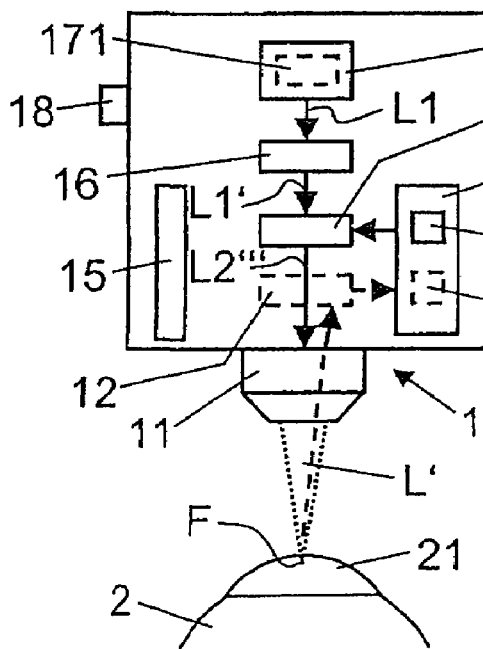
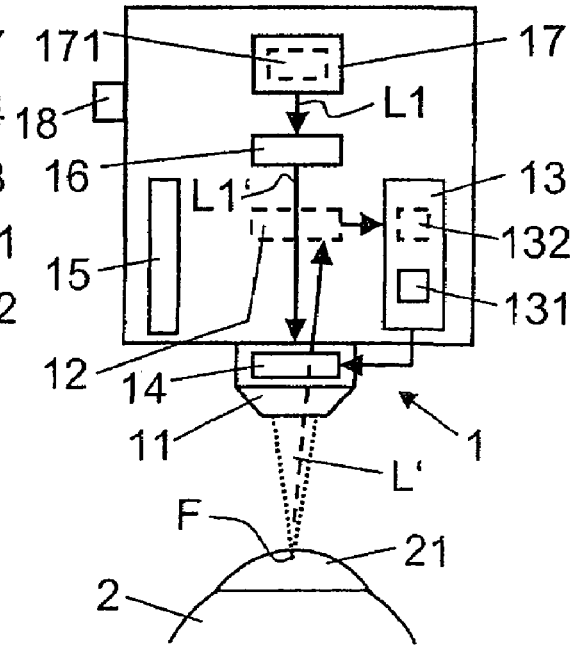
Fig. 2c  Fig. 2d

OPHTHALMOLOGICAL DEVICE

TECHNICAL FIELD

The present invention relates to an ophthalmological device for projecting femtosecond laser pulses. The present invention relates, in particular, to an ophthalmological device with an optical light projection module for projecting deflected femtosecond laser pulses onto a defined treatment surface into an image area extending from the optical axis of the light projection module.

PRIOR ART

Simple spherical lenses focus at the focal point only monochromatic light beams which run near the optical axis (paraxial beams). Beams running that are further removed from the optical axis are focused at another focal point. This most common image error is termed aperture error, or else spherical aberration. If the aim is to focus with a high numerical aperture in order to attain small spot sizes, it is possible to compensate these errors by aspheric lens shape, for example. This compensation provides no assistance for imaging locations lying off the optical axis. In addition, further aberrations such as coma, field curvature, astigmatism or distortions result during optical imaging. Furthermore, axial and lateral chromatic aberrations occur when polychromatic light is being used.

It is normal to use a combination of a number of spherical lenses with different refractive properties to compensate these errors. Diffractive optical elements are also used for this purpose in a few cases. In general, the outlay on correction, and thus the number of optical elements (for the most part lenses and mirrors) and materials which are used rises with the numerical aperture and the field size (size of the sharply focused image area). However, the diameter and the weight of the optical systems also rise substantially with the numerical aperture and the field size. When the focal plane is additionally to be adjusted, the outlay on equipment rises further. This relationship is of great importance particularly in the design of femtolaser systems. For example, femtolaser systems, which have pulse widths of typically 10 fs to 1000 fs (1 fs=$10^{-15}$ s), require numerical apertures of greater than 0.2 in an ophthalmological application, since otherwise the material removal at depth (for example in the cornea) is not accurately defined, and optical breakthrough already comes about partially on structures lying above the focal plane (for example in the epithel). A further undesired phenomenon outside the focal plane are streaky structures (so-called "streaks") in the tissue along the propagation direction of the laser beam. There are breakthroughs above and below the focal plane even in the case of systems with numerical apertures around 0.3. Highly corrected systems with a working area of 10 mm with a numerical aperture of 0.3 require as many as ten and more lenses with a diameter of about 100 mm. Raising the numerical aperture is possible in practice only in conjunction with a reduced image field (image area). In addition, in the case of phases of femtosecond laser pulses which are affected by aberrations, there is the problem that not all light beams come into focus at the same instant, because of different transient times. Particularly in the case of very short pulses, the maximum intensity at the focus is therefore reduced.

By way of example, Patent Application EP 1486185 describes such an ophthalmological device with an application head which can be used manually, and in this case the advantages of the small overall size and the low weight are bought at the expense of the disadvantage of a restricted image field. Patent Application DE 10358927 describes a laser device for material machining by means of laser radiation, in particular for refractive surgery on the human eye by means of deflected femtosecond laser pulses. The device according to DE 10358927 comprises a pulse selection device which modifies selected laser pulses such that the modified pulses either no longer pass into the material to be machined at all, or can at least no longer produce an optical breakthrough there. The modification of the laser pulses comprises influencing parameters such as phase, amplitude, polarization, beam direction and field distribution over beam cross section (beam profile). By means of wavefront modification, in particular, the selected laser pulses are defocused such that the energy density no longer suffices for optical breakthroughs. The pulse selection, and thus the modification, perform, in particular, in a fashion synchronized with the deflection rate.

SUMMARY OF THE INVENTION

It is an object of the present invention to propose an ophthalmological device for projecting deflected femtosecond laser pulses which does not have the disadvantages of the prior art. In particular, it is an object of the present invention to propose an ophthalmological device for projecting deflected femtosecond laser pulses which enable an enlarged image field in the case of a given projection optics, known from the prior art, in conjunction with retention of the central image quality even in the edge regions of the treatment surface (for example focal plane). It is, in particular, a further object of the present invention to propose an ophthalmological device which is of such a small design and such a low weight that it is suitable for manual application and positioning.

Furthermore, the aim is to enable the use of different applanation elements and/or interchangeable objectives through the possibility of being able to adapt the optics.

In accordance with the present invention, these objects are achieved, in particular, by means of the elements of the independent claims. Further advantageous embodiments proceed, furthermore, from the dependent claims and the description.

The ophthalmological device comprises an optical light projection module for projecting deflected femtosecond laser pulses into an image area, extending from the optical axis of the light projection module, on a defined treatment surface.

The abovenamed objects are achieved with the aid of the present invention by virtue, in particular, of the fact that the ophthalmological device is also provided with a controllable optical correction element and a control module connected thereto, the controllable optical correction element being set up to modulate the wavefront of the femtosecond laser pulses in a variable fashion, and the control module being set up to control the correction element as a function of a deflection of the femtosecond laser pulses in such a way that the femtosecond laser pulses are focused in the image area. The controllable optical correction element and the control module are preferably set up to modulate the wavefront of the femtosecond laser pulses sequentially in each case for an image point lying inside the image area and onto which the deflected laser beam is projected. The sequential correction of the wavefront is performed image point by image point, in accordance with the scanning pattern of the deflected laser pulses, and is significantly less complex and complicated than a correction of an overall image with a multiplicity of image points which are to be projected simultaneously into the image area. The controlled modulation of the wavefront enables the focused projection of the femtosecond laser pulses onto the treatment surface in the entire extended image area arranged about the optical axis of the light projection module. The modulation of the wavefront enables even femtosecond laser pulses from pulsed laser beams which run that run at a distance from the optical axis of the light projection module to be imaged onto the machine surface in a fashion focused in the image area. It is possible by means of the adaptive and dynamic modulation of the wavefront of the deflected femtosecond laser pulses for the femtosecond laser pulses to be focused onto the treatment surface in an enlarged image area in conjunction with unchanged projection optics of the light projection module and so the image field can be enlarged in conjunction with an unchanging compact design of a light projection module suitable for manual application. The image quality of the optics of the light projection module can be generally improved by means of the corrective modulation of the laser pulse wavefronts. The controlled modulation of the wavefronts enables the more cost effective provision of a highly compensated optical system with a relatively small number of optical elements, a design that is smaller overall and a lesser resulting weight than optical systems of the prior art. In particular, the controlled correction module enables an ophthalmological device to be designed with a compact, manually positionable light projection module which is not felt to the patient to be threateningly large and has an image field of at least 10 mm and a numerical aperture of at least 0.3. Smaller image fields or image areas, for example with the diameter of 1-2 mm, 3-5 mm or 6-9 mm, can, in particular, be achieved with the design which is further reduced and yet more compact. Moreover, inaccuracies in fabrication and assembly, as well as aberrations can be compensated by means of lightweight optical superstructures in conjunction with regulated operation.

In one variant design, the ophthalmological device comprises a detector module with a wavefront detector and/or a light beam profile detector for determining a wavefront profile or a light beam profile of the femtosecond laser pulses, and the control module is set up to control the correction element as a function of the specific wavefront profile or light beam profile. The wavefront of the femtosecond laser pulses can be dynamically modulated, and therefore dynamically detected for focusing the femtosecond laser pulses in the image area by means of controlling the correction element on the basis of the detected wavefront profile or light beam profile.

In a further variant design, the ophthalmological device comprises optical elements for detecting the femtosecond laser pulses projected into the image area, and the control module is set up to control the correction element as a function of detected femtosecond laser pulses projected into the image area. The detection of the femtosecond laser pulses projected into the image area permits the projection quality actually produced in the image area, for example with the assistance of the abovementioned detector module, to be fed back and determined in a fashion as free from error as possible.

In one variant design, the ophthalmological device comprises optical elements for simulating a reference beam path corresponding to a beam path used for projecting the femtosecond laser pulses onto the treatment surface, and for detecting femtosecond laser pulses projected in the reference beam path. In addition, the control module is set up to control the correction element as a function of detected femtosecond laser pulses projected in the simulated beam path. The detection of the femtosecond laser pulses projected in the reference beam path permits the projection quality to be fed back and determined, for example with the aid of the abovementioned detector module, without intervening (that is to say inserting optical elements) in the beam path used for the machining.

In one variant design, the ophthalmological device comprises a laser source for generating a reference laser beam, and the control module is set up to control the correction element as a function of the reference laser beam deflected and projected in accordance with the femtosecond laser pulses. Depending on the variant, the reference beam path is led via the beam path used for the machining or the reference beam path.

In one variant design, the control module comprises control data with an assignment of control values to deflection values, and the control module is set up to control the correction element on the basis of the control values which are assigned to current deflection values. The control based on defined control data enables, inter alia, a control without feedback based on knowledge of the geometry of the ophthalmological device.

In one variant design, the ophthalmological device comprises optical elements for detecting the femtosecond laser pulses projected into the image area, and a calibration module for generating and storing the control data as a function of detected femtosecond laser pulses projected into the image area. In one variant, the calibration module is set up to generate the control data as a function of the wavefront profile or light beam profile determined by the detector module. By means of the calibration, the control data can, on the one hand, be readjusted and, on the other hand, be adapted upon application to circumstances and requirements specific to machining.

In a number of variant designs, the optical correction element is set up such that during the modulation of the wavefront of the femtosecond laser pulses it varies phase distribution, amplitude distribution, polarization distribution and/or propagation directions in the beam cross section of the femtosecond laser pulses.

In a further variant design, the ophthalmological device comprises a holding element for changeably holding at least one objective element of the optical light projection module. The holding element enables, for example, the interchanging of the entire light projection module or of an objective or objective element (for example one or more lenses) of the light projection module. In particular, the holding element enables the holding or the interchanging of various light projection modules, objectives or objective elements, which are set up for the (focused) projection of deflected femtosecond laser pulses into image areas of different size and/or onto various treatment surfaces, which machine surfaces are, for example, defined (that is to say shaped) by various contact elements to be flat (applanation surface) or curved (spherically, convexly). The controllable optical correction element and the control module are, moreover, set up to modulate the wavefront of the femtosecond laser pulses such that projection errors resulting from the mechanical interchange of the light projection modules, objectives or objective elements are compensated or corrected.

In a number of variant designs, the optical correction element comprises a deformable mirror, a spatial transient time delay element, moveable lenses, moveable prisms, a diffractive optical element, and an anamorphotic optical module, a photonic crystal, a lens array, a spatial polarization plate, a diaphragm and/or a spatial light modulator.

BRIEF DESCRIPTION OF THE DRAWINGS

A design of the present invention is described below with the aid of an example. The example of the design is illustrated by the following attached figures:

FIG. 1a shows a block diagram which diagrammatically illustrates an ophthalmological device being used to treat an eye by means of a focused pulsed laser beam.

FIG. 1b shows a plan view of a treatment surface, machined by the ophthalmological device, and an image area lying thereupon.

FIGS. 2a, 2b, 2c and 2d respectively show a block diagram which diagrammatically illustrates a variant design of the ophthalmological device being used to treat an eye by means of a focused pulsed laser beam.

WAYS OF IMPLEMENTING THE INVENTION

Figure 3A:
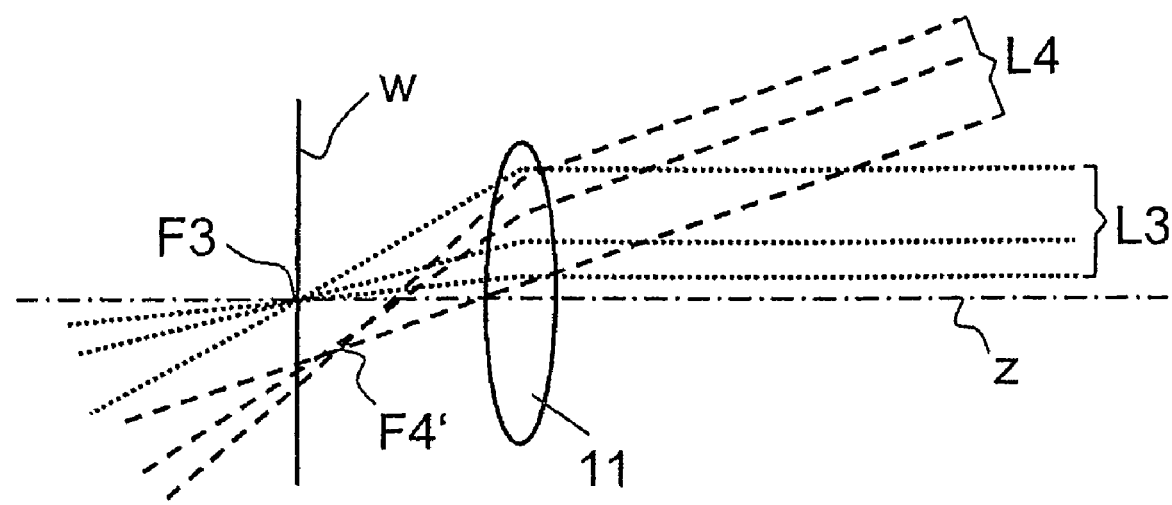
FIG. 3a shows two pulsed laser beams of which the laser beam running further removed from the optical axis is not imaged in a focused fashion onto a treatment surface.

In FIGS. 1a, 2a, 2b, 2c and 2d, the reference symbol 1 denotes an ophthalmological device or an ophthalmological device arrangement with a laser source 17 and an optical light projection module 11, optically connected to the laser source 17, for generating and projecting in a focused fashion a pulsed laser beam L' for the punctiform breakdown of tissue at a focus F (focal point) in the interior of the eye tissue 21, for example in the cornea. The laser source 17 comprises, in particular, a femtosecond laser for generating femtosecond laser pulses which have pulse widths of typically 10 fs to 1000 fs (1 fs=$10^{-15}$ s). The laser source 17 is arranged in a separate housing or in a housing common to the light projection module 11. For the purpose of holding and applying the ophthalmological device 1 or the optical light projection module 11 manually, the ophthalmological device 1 has a diagrammatically illustrated handle 18. As is also illustrated diagrammatically in FIG. 1a, the ophthalmological device 1 comprises a holding element 19 for interchangeably holding various optical light projection modules 11 or at least various objective element(s) of the light projection module 11. The holding element 19 is designed, for example, as a bayonet catch or screw plug.

For the purpose of better understanding, it is to be stated here that FIGS. 1a, 2a, 2b, 2c and 2d illustrate the ophthalmological device 1 diagrammatically and in a simplified fashion. For example, the figures do not reproduce precisely that the optical light projection module 11 has a high numerical aperture of, for example, at least 0.3, that the ophthalmological device 1 is fastened on the eye 2 by means of a suction ring, and that the ophthalmological device 1 comprises a contact element (for example an applanation element) for the contact based deformation (for example for applanation) of the eye 2 when the ophthalmological device 1 is being applied.

As is illustrated diagrammatically in FIG. 1a, the ophthalmological device 1 comprises a deflection module 16, that is to say an optical scanning module or scanner module which is set up to deflect the femtosecond laser pulses L1 generated by the laser source 17 in at least one direction, and thereby to move the focus F of the pulsed laser beam L' in accordance with a scanning pattern (scan pattern) at least in one direction x, y of the (continuous or discontinuous) defined treatment surface w in the tissue 21 of the eye 3. With the motionless light projection module 11 (static), a deflection of the femtosecond laser pulses L effects a movement of the focus F of the pulsed laser beam L' in the image area p which is situated on the treatment surface w and extends from the optical axis z of the light projection module 11 (see FIG. 1b). The image region p is thus scanned image point by image point in accordance with the scanning pattern, individual image points also being able to overlap one another partially or completely. In the applied state of the ophthalmological device 1 or the light projection module 11, the image area p runs substantially normal to the optical axis z, at least at the point of intersection with the optical axis z. It may be maintained here that the treatment surface w and the image area p can be more simply flat, but also curved. The image area p has different possible shapes, depending on the control of the deflection module 16. For example, together with the laser source 17 the deflection module 16 is arranged in a separate housing or in a housing common to the light projection module 11.

In addition, in one variant the ophthalmological device 1 comprises a drive module 15 for moving the light projection module 11 along the directions x and/or y and/or a normal to these directions (for example along the optical axis z). Thus, the drive module 15 can likewise move the focus F of the pulsed laser beam L' in one or more directions. The focus F of the pulsed laser beam L' can also form the normal (z) by means of moveable lenses, for example inside the light projection module 11.

As is illustrated in FIG. 1a, the ophthalmological device 1 additionally comprises a controllable optical correction element 14 which is arranged in the diagrammatically illustrated beam path L between the laser source 17 and the exit of the light projection module 11. The optical correction element 14 is set up for the variable modulation of the wavefront of the femtosecond laser pulses. The phase transient times and/or the propagation directions are varied over the beam cross section of the femtosecond laser pulses by the controllable modulation of the wavefront. Furthermore, the polarization and the amplitude distribution can be varied. Since, given an unchanged spectral distribution, the wavefront can be dependent in general on the amplitude distribution, the polarization distribution and the phase distribution in the beam cross section, or can be influenced by these, it is intended below to talk of a wavefront modulation in place of amplitude, polarization and phase modulation. The term wavefront modulation further comprises the modulation of the propagation directions. The optical correction element 14 is designed, for example, as a deformable mirror, as a spatial transient time delay element, by means of moveable lenses, by means of moveable prisms, and/or as a diffractive optical element. Radially moveable lenses can be integrated, for example, in polar coordinate scanner systems which deflect at a high annular, but comparatively low radial speed. The optical correction element 14 can also be designed by means of an anamorphotic optical module, a chromatic crystal, a lense array, a spatial polarization plate, a diaphragm and/or a spatial light modulator (for example a conventional mirror array or LCD array).

The reference symbol 13 in FIGS. 1a, 2a, 2b, 2c and 2d denotes a control module which is designed by means of software and/or hardware as a programmed logic module. The control module 13 is connected to the optical correction element 14 for the purpose of transmitting control signals. The control module 13 is arranged in a separate housing or in a housing common to the light projection module 11. The control module 13 is set up to control the optical correction element 14 such that the wavefront of the femtosecond laser pulses is modulated so that the deflected femtosecond laser pulses of the pulsed laser beam L' are respectively focused at the image point, this being, specifically, on the treatment surface w for image points inside the entire image area p.

Figure 3B:
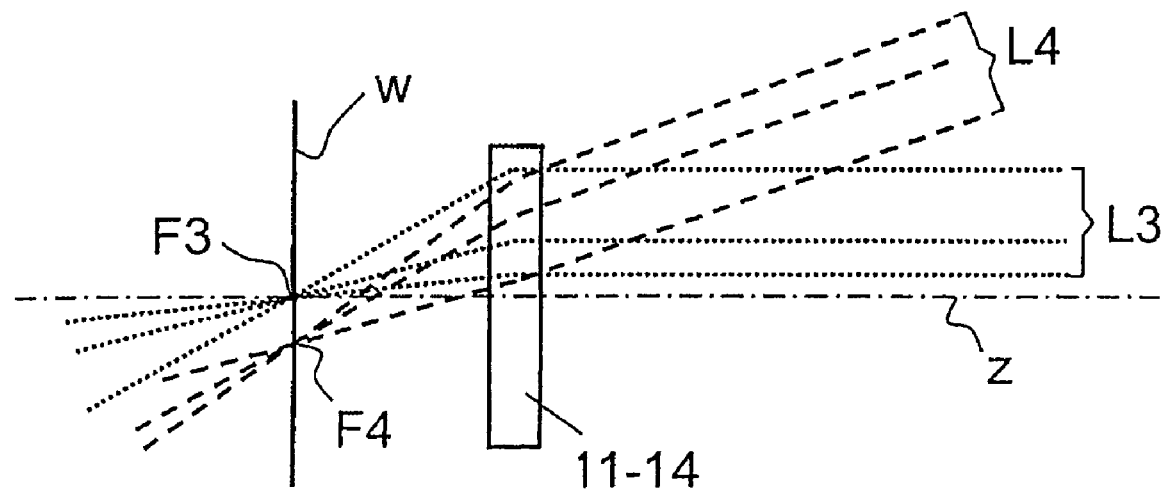
FIG. 3b shows two pulsed laser beams which are both imaged in a focused fashion onto a treatment surface by means of a "corrected" light projection module.

The image of two pulsed laser beams L3, L4 by the "uncorrected" light projection module 11 is illustrated in FIG. 3a. As indicated by the focus F3, the laser beam L3 running in the vicinity of the optical axis z is imaged in a fashion focused onto the treatment surface w. By contrast, the laser beam L4 deflected further from the optical axis z is imaged onto an (unsharp) focal area F4' lying outside the treatment surface w. FIG. 3b illustrates the imaging of the pulsed laser beams L3, L4 by the "corrected" projection system 11-14, which comprises the light projection module 11 and the optical correction element 14, the correction element 14 being controlled by the control module 13 such that the wavefront of the femtosecond laser pulses is modulated such that both the laser beam L3, at the focus F3, and the laser beam L4, at the focus F4, imaged in a fashioned focused onto the image area p of the treatment surface w. The control of the optical correction element 14 is performed independently of the deflection of the femtosecond laser pulses L1, generated by the laser source 17, by the deflection module 16. The deflection of the femtosecond laser pulses L1 is defined, for example, by x/y coordinates in the image area p, or by one or more deflection angles. Data on the deflection are, for example, transmitted by the deflection module 16 to the control module 13, or are already known to the control module 13 from internal control data. In addition, the control of the optical correction element 14 is performed as a function of stored control data 131 and/or feedback relating to the projection of the pulsed laser beam L' in the image area p on the treatment surface w. For the different deflections (deflection values), the control data comprise control values for controlling the optical correction element 14. The control data are permanently defined, for example on the basis of the calculation of the optical system, or of a calibration of the optical system after its assembly, by means of external measuring instruments, or are generated by means of an optional calibration module 132 on the basis of feedback relating to the projection of a laser beam into the image area p on the treatment surface w.

Feedback via the projection into the image area p on the treatment surface w is performed by means of optical elements and of the optional detector module 12. In particular for the purpose of calibration before operational use, the femtosecond laser pulses of the projected laser beam L', or an auxiliary reference laser beam from the optional reference laser source 171, are detected by removable or moveable optical elements, for example mirrors, semitransparent mirrors and/or lenses, at the level of the treatment surface w, and then optically to the detector module 12. For feedback during operational use, the femtosecond laser pulses which are reflected onto the treatment surface w are fed to the detector module 12 via optical elements, for example by means of reflecting and/or semitransparent mirrors and/or lenses. In an alternative variant design, the device 1 comprises optical elements, for example mirrors, semitransparent mirrors and/or lenses, which simulate a reference beam path corresponding to the beam path used for projecting the femtosecond laser pulses onto the treatment surface w such that the detector module 12 can be fed femtosecond laser pulses whose wavefront and/or beam profile correspond to those of femtosecond laser pulses of the laser beam L' in the image area p on the treatment surface w. It will be understood by the person skilled in the art that, as in the case of calibration, feedback during operational use is generated in alternative variant designs on the basis of an additional auxiliary reference laser beam which is generated by the optional reference laser source 171.

In a number of variant designs, the detector module 12 comprises a wavefront detector and/or a light beam profile detector for determining the wavefront profile or the light beam profile of the femtosecond laser pulses fed via the optical elements. The wavefront detector is, for example, designed as a Shack-Hartmann sensor, for example according to US 2003/0038921, or as an interferometer, for example as a shearing interferometer. Further possible embodiments of the wavefront detector are described in Jos. J. Rozema, Dirk E. M. Van Dyck, Marie-José Tassignon, "Clinical comparison of 6 aberrometers. Part 1: Technical specifications", J Cataract Refract Surg, Volume 31, June 2005, pages 1114-1127. The light beam profile detector comprises, for example, a CCD (Charge Coupled Device) chip. The detector module 12 is connected to the control module 13 for feeding back the specific wavefront profile or the light beam profile. The control module 13 is set up to generate control signals on the basis of the feedback, and to lead them to the optical correction module 14 in order to modulate the wavefront of the femtosecond laser pulses by means of the optical correction module 14 such that a desired, defined wavefront profile or a desired, defined light beam profile results in the image area p on the treatment surface w, and the deflected femtosecond laser pulses are adequately focused on the treatment surface w over the entire image area p in accordance with a defined degree of focus. Depending on the machining method, there can be a number of quality criteria for the degree of focus. For example, the maximum intensity at the focus can be defined as degree of focus (important for initiating an optical breakthrough). Furthermore, the shape of the focus (for example circular for a defined machining zone, elliptical as a function of scanning patterns), the diameter thereof (important in the case of uniform spot spacing) or else the intensity profile (for example flat top) can serve as a criterion for the degree of focus. If the focus shape (spot shape) is the decisive criterion, this can be readjusted in the event of an unsatisfactory intensity at the laser source. The readjustment can also be undertaken as a function of the focal position. The readjustment can be required, for example, when the wavefront modulator gives rise to fluctuating intensities.

In the variant design according to FIG. 2a, the controllable optical correction element 14 is inserted into the beam path between the laser source 17 and the deflection module 16. The femtosecond laser pulses L1 generated by the laser source 17 are fed to the correction element 14, which modulates the wavefront of the femtosecond laser pulses L1 in accordance with the control signals of the control module 13, doing so in each case for the image point onto which they are deflected and projected in the image area p. The femtosecond laser pulses L2 generated by the correction element 14 and having a modulated wavefront are fed to the deflection module 16. The deflection module 16 deflects the femtosecond laser pulses L2 in at least one scanning direction. The femtosecond laser pulses L2' deflected by the deflection module 16 are fed to the light projection module 11 for the purpose of focused projection. In the variant design according to FIG. 2b, the controllable optical correction element 14 is integrated in the deflection module 16. The femtosecond laser pulses L1 generated by the laser source 17 are fed to the deflection module 16. In the internal beam path of the deflection module 16, the correction element 14 modulates the wavefront of the femtosecond laser pulses L1 in accordance with the control signals of the control module 13, doing so in each case for the image point onto which they are deflected and projected in the image area p. The femtosecond laser pulses L2" with modulated wavefront, which are modulated by the correction element 14 and deflected by the deflection module 16 in at least one scanning direction, are fed to the light projection module 11 for focused projection.

In the variant design according to FIG. 2c, the controllable optical correction element 14 is inserted into the beam path between the deflection module 16 and the light projection module 11. The femtosecond laser pulses L1', generated by the laser source 17 and deflected by the deflection module 16, are fed to the correction element 14. The correction element 14 modulates the wavefront of the deflected femtosecond laser pulses L1' in accordance with the control signals of the control module 13, doing so in each case for the image point onto which they are deflected and projected in the image area p. The femtosecond laser pulses L2''' with modulated wavefront, which are deflected by the deflection module 16 in at least one scanning direction and are modulated by the correction element 14, are fed to the light projection module 11 for focused projection. In the case of a deflecting mirror in the deflection module 16, said mirror can also simultaneously be designed with a capacity to be deformed or to modulate intensity, and can thus also serve as optical correction element. Furthermore, in addition to correction based on wavefront modulation it is also possible, for example, to use a deformable mirror for adjusting (positioning) the focus.

In the variant design according to FIG. 2d, the controllable optical correction element 14 is integrated in the light projection module 11. The femtosecond laser pulses L1 generated by the laser source 17 are fed to the deflection module 16, which deflects the femtosecond laser pulses L1 in at least one scanning direction. The deflected femtosecond laser pulses L1' are fed to the correction element 14 in the light projection module 11, which modulates the wavefront of the deflected femtosecond laser pulses L1', doing so in each case for the image point onto which they are deflected and projected in the image area p. The femtosecond laser pulses with modulated wavefront, which are generated by the correction element 14, are projected in a focused fashion by the light projection module 11.

The invention claimed is:

1. Ophthalmological device, comprising:
    an optical light projection module for projecting deflected femtosecond laser pulses into an image area, extending from the optical axis of the light projection module, on a defined treatment surface,
    a controllable optical correction element for the variable modulation of the wavefront of the femtosecond laser pulses, and
    a control module connected to the correction element, for controlling the correction element as a function of a deflection of the femtosecond laser pulses in such a way that the femtosecond laser pulses are focused in the extended image area on the defined treatment surface.

2. Device according to claim 1, wherein the controllable optical correction element and the control module are set up to modulate the wavefront of the femtosecond laser pulses sequentially in each case for an image point lying inside the image area.

3. Device according to claim 1, further comprising a detector module comprising at least one of the following: a wavefront detector and a light beam profile detector for determining a wavefront profile or light beam profile of the laser pulses, and wherein the control module is set up to control the correction element as a function of the specific wavefront profile or light beam profile, respectively.

4. Device according to claim 1, further comprising optical elements for detecting the femtosecond laser pulses projected into the image area, and wherein the control module is set up to control the correction element as a function of detected femtosecond laser pulses projected into the image area.

5. Device according to claim 1, further comprising optical elements for simulating a reference beam path corresponding to a beam path used for projecting the femtosecond laser pulses onto the treatment surface, and for detecting femtosecond laser pulses projected in the reference beam path, and wherein the control module is set up to control the correction element as a function of detected femtosecond laser pulses projected in the simulated beam path.

6. Device according to claim 1, further comprising a laser source for generating a reference laser beam, and wherein the control module is set up to control the correction element as a function of the reference laser beam deflected and projected in accordance with the femtosecond laser pulses.

7. Device according to claim 1, wherein the control module includes stored control data with an assignment of control values to deflection values, and in that the control module is set up to control the correction element on the basis of the control values which are assigned to current deflection values.

8. Device according to claim 7, further comprising optical elements for detecting the femtosecond laser pulses projected into the image area, and a calibration module for generating and storing the control data as a function of detected femtosecond laser pulses projected into the image area.

9. Device according to claim 8, further comprising a detector module comprising at least one of the following: a wavefront detector and a light beam profile detector for determining a wavefront profile or light beam profile of the femtosecond laser pulses, and wherein the calibration module is set up to generate the control data as a function of the determined wavefront profile or light beam profile, respectively.

10. Device according to claim 1, wherein the optical correction element is set up such that during the modulation of the wavefront of the femtosecond laser pulses it varies at least one of the parameters comprising phase distribution, amplitude distribution, polarization distribution and propagation directions in the beam cross section of the femtosecond laser pulses.

11. Device according to claim 1, wherein the optical correction element comprises at least one of the following: deformable mirror, spatial transient time delay element, moveable lenses, moveable prisms, diffractive optical element, anamorphotic optical module, photonic crystal, lens array, spatial polarization plate, diaphragm and spatial light modulator.

12. Device according to claim 1, further comprising a handle for manually holding and applying the ophthalmological device, and wherein the optical light projection module has a numerical aperture of at least 0.3, and in that the image area on the treatment surface has a diameter of at least 10 mm.

13. Device according to claim 1, further comprising a holding element for changeably holding at least one objective element of the optical light projection module.

* * * * *